United States Patent [19]

Gornowicz et al.

[11] Patent Number: 4,705,877

[45] Date of Patent: Nov. 10, 1987

[54] NOVEL AMINOHYDROCARBYL-SUBSTITUTED KETOXIMOSILANES

[75] Inventors: Gerald A. Gornowicz; Chi-Long Lee, both of Midland, Mich.

[73] Assignee: Dow Corning Corporation, Midland, Mich.

[21] Appl. No.: 18,674

[22] Filed: Feb. 25, 1987

[51] Int. Cl.$^4$ ............................................... C07F 7/10
[52] U.S. Cl. .................................................... 556/422
[58] Field of Search ......................................... 556/422

[56] References Cited

U.S. PATENT DOCUMENTS 2,672,473  3/1954  Sommer ............................. 556/422
3,146,250  8/1964  Speier ............................... 260/448.2
3,189,576  6/1965  Sweet ................................ 260/46.5
3,674,738  7/1972  Nitzsche et al. ................. 556/422 X
3,697,568  10/1972  Boissieras et al. ................ 556/422

FOREIGN PATENT DOCUMENTS 57-16893  1/1982  Japan ................................. 556/427
60-4837   2/1985  Japan ................................. 556/422

Primary Examiner—Paul F. Shaver
Attorney, Agent, or Firm—Robert Spector

[57] ABSTRACT

This invention pertains to novel silanes wherein the silicon atom is bonded to at least one ketoximo group and a carbon atom of a primary or secondary amino group. The remaining substituents on the silicon atom are alkoxy groups and/or monovalent hydrocarbon radicals.

4 Claims, No Drawings

NOVEL AMINOHYDROCARBYL-SUBSTITUTED KETOXIMOSILANES

BACKGROUND OF THE INVENTION

1. Field of the Invention

This invention pertains to novel organosilicon compounds. More particularly, this invention pertains to a novel ketoximosilanes containing an amino group that is separated from the silicon atom by at least one carbon atom.

2. Description of the Prior Art

Silanes containing two or more ketoximo groups bonded to silicon are known in the art, U.S. Pat. No. 3,189,576, which issued to Sweet on June 15, 1965, teaches preparing silanes corresponding to the formula

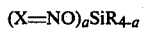

by reacting a ketoxime of the formula X=NOH with a chlorosilane of the formula $Cl_aSiR_{4-a}$ in the presence of an acid acceptor. The number of moles of ketoxime is at least equal to the number of moles of chlorine present in the silane. In these formulae X= represents $R'_2C=$ or $R''C=$, where $R'$ represents a monovalent hydrocarbon radical or a monovalent halogenated hydrocarbon radical. R is selected from the group consisting of $R'$, cyanoalkyl radicals and the hydrogen atom, and $R''$ represents a divalent hydrocarbon radical or a divalent halogenated hydrocarbon radical and a is 1, 2, 3, or 4.

The ketoximosilanes described by Sweet are useful curing agents for one-part moisture curable polyorganosiloxane compositions.

Japanese examined application No. 4837/85. which issued on Feb. 6, 1985, describes a method for preparing ketoximosilanes of the formula $R_aSi(NR'_2)_b(ON=X)_{4-a-b}$ by the reaction of an alkylaminosilane of the general formula $R_aSi(NR'_2)_{4-a}$ with a ketoxime of the formula X=NOH, where R represents an optionally substituted monofunctional aliphatic, alicyclic or aromatic hydrocarbon radical, $R'$ is R or hydrogen, X is as defined hereinabove for the compounds of the aforementioned Sweet patent, a is 0 or 1, b is 0, 1, 2, or 3, and the sum of a and b is at most 3.

The silicon-nitrogen bond of the ketoximosilanes disclosed in the aforementioned Japanese patent publication would be expected to be unstable due to the relative ease with which a silicon-nitrogen bond can be hydrolyzed.

For some end use applications it would be desirable to have a ketoximosilane containing a primary or secondary amino group that is bonded to silicon through carbon rather than through nitrogen as in the compounds of the aforementioned Japanese patent publication. The amino group would provide the means to incorporate a ketoximosilyl group into organic polymers and silicone/organic copolymers containing amine-reactive groups such as isocyanate. The resultant polymers could be cured in the presence of atmospheric moisture.

An objective of this invention is to provide aminohydrocarbyl-substituted ketoximosilanes. A second objective is to provide methods for preparing these novel organosilicon compounds.

SUMMARY OF THE INVENTION

This invention provides novel silanes wherein the silicon atom is bonded to (1) at least one ketoximo group and (2) a carbon atom of a primary or secondary amino group. These silanes can be reacted with polymers containing amine-reactive functional groups to prepare moisture curable compositions.

DETAILED DESCRIPTION OF THE INVENTION

The novel silanes of this invention are represented by the general formula

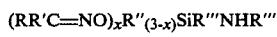  I where R and $R'$ represent identical or different monovalent hydrocarbon radicals, $R''$ represents a monovalent hydrocarbon radical, a monovalent fluorinated hydrocarbon radical, or an alkoxy group containing from 1 to 4 carbon atoms, with the proviso that when more than one $R''$ substituent is present these substituents can be identical or different, $R'''$ represents a divalent hydrocarbon radical, $R''''$ represents a monovalent hydrocarbon radical or a hydrogen atom, and x represents the integer 1, 2 or 3.

One method for preparing the silanes of this invention, referred to hereinafter as method 1, is by reacting a silane of the formula $R''_3SiR'''NHR''''$, where at least one of the substituents represented by $R''$ is an alkoxy group containing from 1 to 4 carbon atoms, with at least an equimolar amount of a ketoxime of the formula $RR'C=NOH$. During this reaction one or more of the alkoxy groups present on the initial silane is replaced by a ketoximo group, $RR'C=NO-$, forming the corresponding alcohol $R''H$ as a by-product. Because this reaction is believed to involve an equilibrium, the by-product alcohol should be continuously removed from the reaction to favor formation of the desired ketoximosilane.

The reaction mixture preferably contains a liquid organic diluent that forms an azeotrope with the by-product alcohol to facilitate removal of the alcohol from the reaction mixture at temperatures from about 50 to about 150 degrees C.

Monoketoximosilanes wherein the divalent hydrocarbon radical represented by $R'''$ is alkylene and contains from 3 to about 6 carbon atoms can be prepared by reacting the desired ketoxime with a cyclic silylamine of the formula

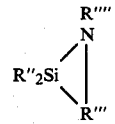  II

This method will be referred to hereinafter as method 2. This method is characterized by displacement of the silicon bonded nitrogen atom by the oxygen atom of the ketoxime. The reaction is sometimes exothermic, however to ensure completeness of the reaction and maximize yields the reaction mixture should be heated at a temperature of from about 40 to about 100 degrees C. for a period of from 30 minutes to several hours, depending on the amounts of reactants used.

Cyclic silylamines represented by formula II are described in U.S. Pat. No. 3,146,250, which issued to Speier on Aug. 25 1964. These compounds are prepared by reacting a haloalkylhalosilane of the formula $R''_2Si(R'''X)X$ where the two substituents represented by X are chlorine, bromine or iodine, with a stoichiometric excess of a primary amine of the formula H₂NR'''' where R''' represents an alkylene radical containing from 3 to 6 carbon atoms. The reaction is preferably conducted in the presence of a basic material such as a tertiary amine to react with the hydrogen halide generated as a by-product of the reaction.

As used herein to define the substituents represented by R, R', R'' and R'''', the term "monovalent hydrocarbon radical" includes hydrocarbon radicals containing from one up to twenty or more carbon atoms. These radicals can be alkyl such as methyl, ethyl, n-propyl, iso-propyl, butyl, decyl and dodecyl; cycloalkyl such as cyclohexyl, aryl such as phenyl and naphthyl, alkaryl such as tolyl or aralkyl such as benzyl. When R'' represents a fluorinated monovalent hydrocarbon radical, it contains from 3 to 20 carbon atoms.

When a monovalent hydrocarbon radical is alkyl it preferably contains from 1 to about 10 carbon atoms, most preferably from 1 to 4 carbon atoms. The preference for certain hydrocarbon radicals as substituents on the present silanes is based on the availability of the intermediates used to prepare the reactants containing these substituents. For the same reason cyclohexyl is the preferred cycloalkyl radical, phenyl is the preferred aryl radical and in those instances when the substituent represented by R'' is a fluoroalkyl radical, it is preferably 3,3,3-trifluoropropyl.

The divalent hydrocarbon radical represented by R''' can contain from one up to about twenty carbon atoms, R''' can be alkylene such as methylene, ethylene, butylene, or dodecylene, cycloalkylene such as cyclohexylene or arylene such as phenylene. This radical is preferably alkylene containing from 1 to about 5 carbon atoms or phenylene, this preference being based on the availability of the intermediates used to prepare the corresponding halohydrocarbylsilane that is, in turn, the compound typically reacted with ammonia or a primary amine to obtain the organosilicon starting material for the present silanes.

Representative alkoxysilanes that can be reacted with a ketoxime to prepare the silanes of this invention in accordance with the aforementioned method 1 include but are not limited to
dimethylmethoxy-3-aminopropylsilane
dimethylmethoxy-4-aminocyclohexylsilane
methyldimethoxy-4-aminobutylsilane
methyldimethoxy-p-aminophenylsilane
methyldimethoxy-3-aminopropylsilane
trimethoxy-3-aminopropylsilane
dimethylmethoxy-p-aminophenylsilane
diethylmethoxy-3-aminopropylsilane
ethyldiethoxy-4-aminobutylsilane
phenyldimethoxy-3-aminopropylsilane
3,3,3-trifluoropropylmethylmethoxy-3-aminopropylsilane
n-butylmethylmethoxy-3-aminopropylsilane and cyclohexyldimethoxy-3-aminopropylsilane The cyclic silylamines that are reacted to prepare the present compounds in accordance with the aforementioned method 2 correspond the preceding formula II. One of the reactants used to prepare these silylamines is a primary amine. Representative amines of this type include methylamine, ethylamine, n-propylamine, n-butylamine, n-octylamine, aniline and benzylamine.

The other reactant for preparing silanes used in method 2 is a silane containing a silicon bonded chlorine, bromine or iodine atom and a second chlorine, bromine or iodine atom that is part of a silicon bonded monohaloalkyl radical wherein the halogen atom is separated from the silicon atom by an acyclic series of from 3 to 6 carbon atoms. The two remaining substituents on silicon are preferably monovalent hydrocarbon radicals, most preferably methyl, phenyl or 3,3,3-trifluoropropyl radicals Representative ketoximes that are reacted with silanes in accordance with either of the two procedures described in the preceding paragraphs include
acetone ketoxime
methylethyl ketoxime
diethyl ketoxime
phenylethyl ketoxime
diphenyl ketoxime
benzophenone ketoxime
methylisopropyl ketoxime
methylisobutyl ketoxime and
cyclohexylmethyl ketoxime Because the present ketoximosilanes will undergo hydrolysis in the presence of even trace amounts of moisture these compounds should be prepared and stored under anhydrous conditions. The reactions used to prepare the compounds are preferably conducted under an inert atmosphere such as nitrogen.

The following examples describe preferred embodiments of the present silanes and preparative methods, and should not be interpreted as limiting the scope of the accompanying claims. All parts and percentages in the examples are by weight unless otherwise indicated.

EXAMPLE 1

A glass reactor equipped with a magnetically activated stirrer was purged with dry nitrogen and then charged with 143 grams (1 mole) of a silane corresponding to the formula

(III)

The reactor was then sealed using a rubber septum. A 90 gram (1 mole) quantity of methylethylketoxime was then added to the reactor by injecting it through the rubber septum. The resultant mixture was then heated until the temperature of the mixture reached 70 degrees C.

The infra-red absorption spectrum of the resultant reaction product did not exhibit the strong, broad absorption at 3250 cm$^{-1}$ that is characteristic of the =NOH group. A strong absorption at 910 cm$^{-1}$ and a weaker absorption characteristic of the =NH group were present in the spectrum of the reaction product but not in either of the starting materials. Finally, a strong absorption characteristic of the silane represented by formula III was absent in the reaction product.

The nuclear magnetic resonance spectrum of the reaction product showed the following absorptions, reported in ppm downfield from tetramethylsilane: a singlet at 0.11 ppm. corresponding to the six hydrogens present in the two silicon bonded methyl radicals; an absorption at 1.73 ppm assigned to N=CCH3; and complex absorptions within the range from 1.8 to 2.4 ppm. assigned to the hydrogen atoms present in the —NCH3, CCH2C=N, and CCH2N groups. The spectrum was similar to one obtained for tris(methylethylketoximo)methylsilane.

These data indicate that the initial reactants had been consumed to form a compound of this invention represented by the formula.

(MeEtC=NO)(Me)$_2$SiCH$_2$CH(Me)CH$_2$N(H)Me where Me represents methyl and Et represents ethyl.

EXAMPLE 2

A glass reactor equipped with a mechanically driven stirrer and a distillation column was purged with dry nitrogen and charged with 179 grams (1 mole) of dry trimethoxy-3-aminopropylsilane, at which time 360 grams (4 moles) of dry methylethylketoxime were added. The temperature of the reaction mixture rose spontaneously to 35 degrees C. A 200 cc. portion of toluene was then added and the reaction mixture was heated at the boiling point, during which time 103 grams of volatile materials were removed by distillation within the range of from 70 to 100 degrees C. An additional 50 cc. of toluene were then added and the reaction mixture was again heated at the boiling point with distillation of volatile material. The weight of volatile material removed within the range of from 100 to 110 degrees C. was 94 grams. Analysis of the combined distillates by gas liquid chromatography indicated the presence of approximately 74 grams (2.3 moles) of methanol.

The residue remaining in the reactor was concentrated under reduced pressure (0.665-1.33 kilopascals) while being heated until the temperature of the residue reached 125 degrees C. The orange colored residue weighed 287 grams, equivalent to a yield of 97%, based on the initial silane. The nuclear magnetic resonance spectrum of the residue indicated that it consisted essentially of a silane of this invention represented by the formula (MeEtC=O)$_2$(MeO)Si(CH$_2$)$_3$NH$_2$, where Me represents methyl and Et represents ethyl.

The procedure described in the first part of this example was repeated, with the exception that when the vapor temperature reached between 100 and 110 degrees C. during the distillation step 100 cc. of toluene were added and the distillation of volatile material was continued until the temperature of the reaction mixture reached 150 degrees C. under atmospheric pressure. The reaction mixture was allowed to cool to room temperature and the material in the reaction vessel was concentrated by heating it to a temperature of 150 degrees C. under a pressure of 0.665 kilopascals. The nuclear magnetic resonance spectrum of the residue on the reactor agreed with the one calculated for a compound of this invention exhibiting the formula (MeEtC=O)$_3$Si(CH$_2$)$_3$NH$_2$.

That which is claimed is:

1. A silane represented by the formula (RR'C=NO)$_x$R''$_{(3-x)}$SiR'''NHR'''' where R and R' represent identical or different monovalent hydrocarbon radicals, R'' represents a monovalent hydrocarbon radical, a monovalent fluorinated hydrocarbon radical, or an alkoxy group containing from 1 to 4 carbon atoms, with the proviso that when more than one R'' substituent is present these substituents can be identical or different, R''' represents a divalent hydrocarbon radical, R'''' represents a monovalent hydrocarbon radical or a hydrogen atom, and x represents the integer 1, 2 or 3.

2. A silane according to claim 1 where said monovalent hydrocarbon radicals represented by R, R', and R'''' are individually alkyl containing from 1 to 20 carbon atoms, cycloalkyl, or aryl, R'' represents alkyl containing from 1 to 20 carbon atoms or fluoroalkyl containing from 3 to 20 carbon atom, the divalent hydrocarbon radical represented by R''' is alkylene containing from 1 to 20 carbon atoms or phenylene and x is 1 or 2.

3. A silane according to claim 2 where said alkyl and alkylene radicals contain from 1 to 4 carbon atoms, said cycloalkyl radical is cyclohexyl, said aryl radical is phenyl, said fluoroalkyl radical is 3,3,3-trifluoropropyl and any alkoxy radicals represented by R'' are methoxy.

4. A silane according to claim 3 where R, R'''' and at least one of the substituents represented by R'' are methyl, any remaining R'' substituents are methoxy, R' is ethyl and R''' is propylene or —CH$_2$CH(CH)$_3$CH$_2$—.

* * * * *